(12) United States Patent
Baig

(10) Patent No.: US 7,611,525 B2
(45) Date of Patent: Nov. 3, 2009

(54) RETRIEVAL DEVICE

(76) Inventor: Mirza Kamran Baig, 588 Adams Hill, The Laurels, Nottingham (GB) NG7 2GZ (*) Notice: Subject to any disclaimer, the term of this patent is extended or adjusted under 35 U.S.C. 154(b) by 188 days.

(21) Appl. No.: 10/533,009

(22) PCT Filed: Oct. 31, 2003

(86) PCT No.: PCT/GB03/04692

§ 371 (c)(1),
(2), (4) Date: Apr. 28, 2005

(87) PCT Pub. No.: WO2004/039290

PCT Pub. Date: May 13, 2004

(65) Prior Publication Data

US 2006/0030865 A1  Feb. 9, 2006

(30) Foreign Application Priority Data

Nov. 1, 2002  (GB) .................................. 0225427.4

(51) Int. Cl.
 *A61M 29/00*  (2006.01)
 *A61F 2/06*  (2006.01)
(52) U.S. Cl. .................... 606/194; 604/96.01; 623/1.11

(58) Field of Classification Search ................. 606/113, 606/194, 108; 604/96.01; 623/1.11
See application file for complete search history.

(56) References Cited

U.S. PATENT DOCUMENTS

| 4,930,496 | A | * | 6/1990 | Bosley, Jr. ..................... 601/4 |
| 5,868,753 | A | * | 2/1999 | Schatz ........................ 606/108 |
| 5,910,154 | A | * | 6/1999 | Tsugita et al. ............... 606/200 |
| 6,027,509 | A | * | 2/2000 | Schatz et al. ................ 606/108 |

FOREIGN PATENT DOCUMENTS

EP  0364420  4/1990

* cited by examiner

*Primary Examiner*—Julian W Woo
*Assistant Examiner*—Melissa Ryckman
(74) *Attorney, Agent, or Firm*—Andrus, Sceales, Starke & Sawall, LLP

(57) ABSTRACT

A device for retrieval of a foreign body, such as an undeployed stent from a vessel of a patient, has a central shaft for receiving a guidewire therein. A balloon support extends from the central shaft and has a free end carrying an inflatable balloon. The inflatable balloon is arranged to expand inwardly towards the central shaft on inflation, so as in use to bear against the outer circumference of the stent and hold the stent against the central shaft. The combined stent and device can then be withdrawn from the vessel.

11 Claims, 4 Drawing Sheets

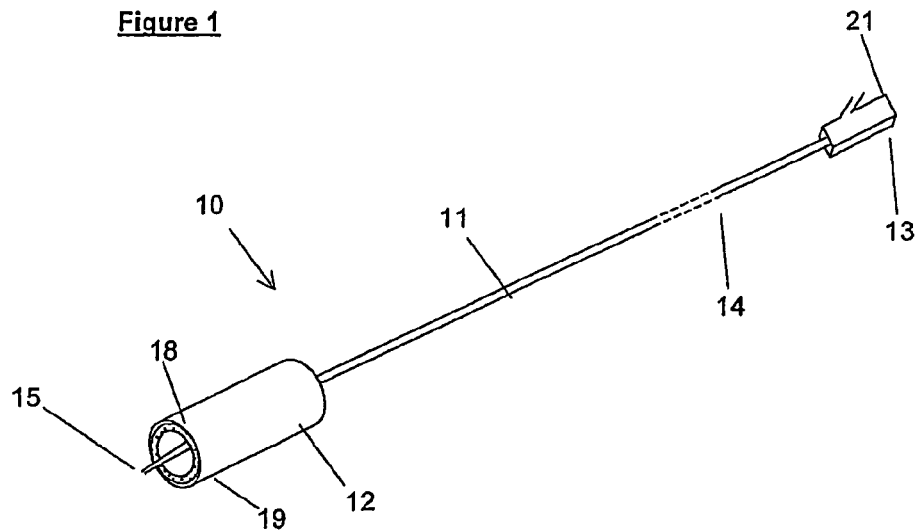
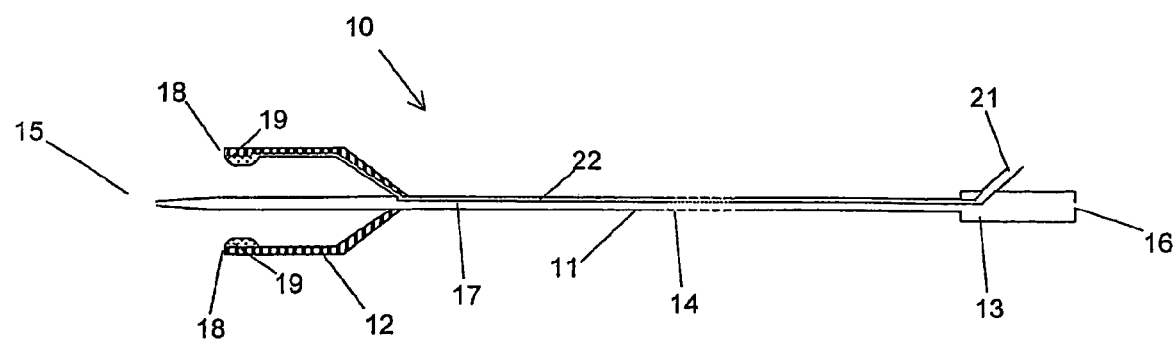

RETRIEVAL DEVICE

CROSS-REFERENCE TO RELATED APPLICATIONS

This application is the U.S. national stage application of International Application PCT/GB2003/004692, filed Oct. 31, 2003, which international application was published on May 13, 2004, as International Publication WO2004/039290 in the English language. The International Application claims priority of United Kingdom Patent Application 0225427.4, filed Nov. 1, 2002.

This invention relates to a device for the retrieval of foreign bodies, such as surgical tools and materials, from a vessel of a patient. Whilst the device of the present invention may be used for the retrieval of substantially all kinds of foreign bodies from substantially all types of vessels, it has been developed particularly for the retrieval of an undeployed stent from a vessel of a patient during an intravascular angioplasty procedure, and will therefore be described herein with particular emphasis on this application.

Intravascular angioplasty is a surgical procedure for the repair of a collapsed or constricted blood vessel. A standard technique is to introduce a balloon-tipped catheter into the vessel, usually along a previously placed guidewire. Once the balloon tip of the catheter has been located at the site of the stricture, or stenosis, it is then inflated thereby dilating the vessel and hence improving blood flow. It is common to treat any residual stenosis in the vessel by placing a stent, usually a perforated metal tube, into the vessel to provide radial support to the vessel wall.

The stent is usually introduced in a compressed, or "undeployed" condition, carried on the deflated balloon of a balloon-tipped catheter. The balloon, which is positioned within the central cavity of the stent, is then inflated so as to expand, or "deploy" the stent at the required site.

However, a problem sometimes encountered with this procedure is that the undeployed stent can become detached from the delivery balloon, and thus becomes a free-floating foreign body within the vessel. Not only can this impede blood flow, and thus cause the vessel to occlude, but also presents the more serious hazard of the stent embolising (floating off) to another part of the body. If the embolised stent should reach a vital organ, the consequences can be dire—for example, a stroke can occur if an embolised stent reaches the brain.

Furthermore, one of the most significant applications of intravascular angioplasty is in the repair of the coronary artery, without the need for open surgery. If an undeployed stent should become detached from its delivery balloon during a coronary angioplasty procedure, it is often necessary to proceed immediately to open surgery in order to remove the stent.

Despite the critical nature of this problem, current techniques for retrieving undeployed stents from a vessel are generally inadequate, and often the only way to ensure retrieval of the stent is by open surgery. Such standard techniques include providing miniature forceps or a so-called "goose neck" snare device at the tip of a catheter, to attempt direct grasping of the stent.

The use of balloon-tipped catheters for retrieval, as well as delivery of stents has also been proposed. However, devices based on this principle tend to require the user to "thread" the deflated balloon back into the central cavity of the undeployed stent, and then to re-inflate it once in position. Such devices are rather awkward to use, and frequently result in the stent being pushed further into the vessel, or deployed at an unintended location in the vessel.

It has now been realised that a solution to this problem is achievable by providing a device having a balloon arranged when inflated to bear against the outer, rather than the inner, circumference of the stent. However, in order to ensure that the captured stent does not become detached from the retrieval device before the device as a whole is withdrawn from the vessel, the device must also have a central component arranged to pass through the cylindrical central cavity of the stent, in order that the inflated balloon can urge the stent thereagainst.

Therefore, according to the present invention, there is provided a device for retrieval of a foreign body from a vessel of a patient, which device comprises: a flexibly resilient central shaft having an axial channel for receiving a guidewire therein; balloon support means extending from the central shaft and having a free end spaced therefrom; and inflatable balloon means provided at said free end and arranged to expand inwardly towards the central shaft upon inflation; whereby in use the device is positioned such that a foreign body to be retrieved is located between said free end and said central shaft, and the balloon means is subsequently inflated to bear against the foreign body and hold it against the central shaft, such that the combined foreign body and device can be withdrawn from the vessel.

According to a preferred embodiment of the present invention, there is provided a device for retrieval of an undeployed stent from a vessel of a patient, which device comprises: a central shaft having an axial channel for receiving an angioplasty guidewire therein; balloon support means extending from the central shaft and having a free end spaced therefrom; and inflatable balloon means provided at said free end and arranged to expand inwardly towards the central shaft upon inflation; whereby in use the device is positioned such that an undeployed stent is located between said free end and said central shaft, and the balloon means is subsequently inflated to bear against the outer circumference of the stent and hold the stent against the central shaft, such that the combined stent and device can be withdrawn from the vessel.

It will be appreciated that the inflatable balloon means must be arranged so as in use to bear against the stent in at least two locations around its circumference, so that the stent is grasped by the balloon means on inflation. For example, this may be achieved by the provision of two or more separate balloon means carried on the free end of two or more balloon support means at spaced intervals around the central shaft. However, it is preferred that there should be only one inflatable balloon means, having a generally annular shape, such that on inflation the balloon means bears against the entire outer circumference of the stent.

Similarly, while the balloon support means might feasibly comprise two or more elements arranged at spaced intervals around the central shaft, it is preferred that the balloon support means should take the form of a generally cylindrical tube or sleeve, surrounding the central shaft and extending generally axially relative thereto.

The free end of the balloon support means thus takes the form of a rim of the tube or sleeve, said rim being generally circular and having the central shaft passing through its centre. In embodiments where the balloon support means is other than a tube or sleeve, it is nevertheless preferred that the free end should be a rim. In embodiments where the balloon support means comprise one or more separate elements, it is preferred that the free ends of those elements should be one or more rim members defining a notional rim around the central shaft.

The central shaft is preferably of a generally cylindrical construction, having a uniform diameter along most of its length, but with a short tapering portion towards its tip. The diameter of the shaft should be as small as is practicable, in order that it can be fed into the cylindrical central cavity of the stent. In preferred embodiments, the tip extends beyond the free end of the balloon support means.

The device preferably has a hub at the end of the central shaft distal from the sleeve, the mouth of the sleeve being directed away from the hub. A port is provided on the hub, which is in fluid communication with the balloon, preferably by means of an inflation tube passing along the axial channel in the central shaft and into the balloon support means. Inflation of the balloon may therefore be effected by the injection of an inflation fluid through the port.

The port is preferably adapted to receive a syringe from which substantially 2 to 5 ml of inflation fluid can be injected to inflate the balloon. In order that the progress of the surgical procedure may be followed by standard radiographic techniques, it is much preferred that the inflation fluid is of radiographic contrast.

Once the device of the present invention has been used to capture a free-floating stent, it is desirable that the combined device and stent assembly should be capable of being withdrawn quickly and easily from the vessel of the patient. Consequently, it is preferred that the device should be adapted for delivery into and recovery from a vessel by means of a guiding catheter, which may be of a standard construction.

The guiding catheter will often already be in place, having been used previously for the introduction of the stent itself and other tools used in the angioplasty procedure. Similarly, the guiding catheter and the angioplasty guidewire will usually be retained in position following retrieval of the undeployed stent, in order to continue the angioplasty procedure.

In an alternative embodiment of the present invention, there is provided a kit of parts comprising a retrieval device as hereinbefore described, and further comprising a guiding catheter for delivery of the device into a vessel, and subsequent recovery of the device therefrom.

In order that the present invention may be more clearly understood, a preferred embodiment will now be described in detail, though only by way of example, with reference to the following drawings, in which:

FIG. 1 is a perspective view of a retrieval device according to the present invention;

FIG. 2 is a cross-sectional side view of the retrieval device of FIG. 1; and

Figure 3:
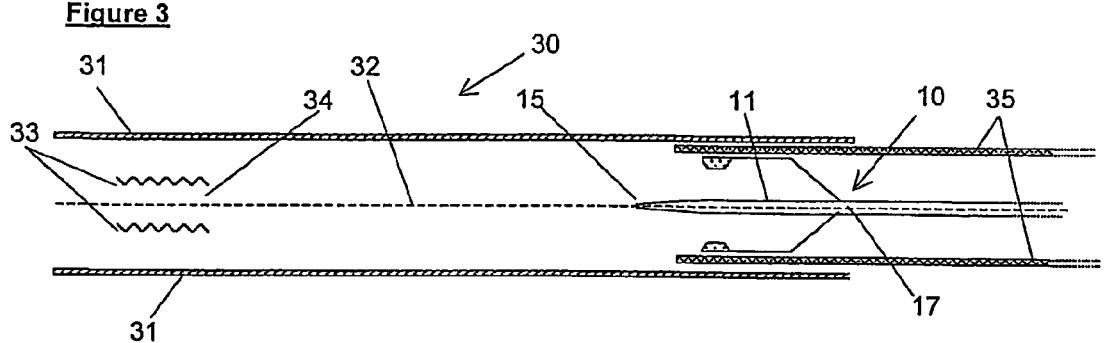
FIGS. 3 to 9 are an illustrative sequence showing the retrieval device of FIGS. 1 and 2 being used to remove an undeployed stent from a vessel of a patient.

Referring first to FIGS. 1 and 2, there is shown a retrieval device according to the present invention, generally indicated 10. The device 10 comprises a flexibly resilient central shaft 11 having a generally cylindrical sleeve 12 at one end thereof, and a hub 13 at the other end thereof. The central shaft 11 will in practice be considerably longer than shown here, as indicated at 14. The shaft 11 is generally cylindrical along its length, and tapers towards a tip 15 having an aperture therein allowing access to a channel 17 running axially along the length of the shaft 11. A further aperture 16 is provided at the other end of the shaft 11, also in communication with the channel 17.

The sleeve 12 extends axially relative to the central shaft 11 and has a free end defining a circular rim 18 having the central shaft 11 at its centre. The tip 15 of the central shaft 11 extends beyond the rim 18. The rim 18 acts as a support means for a generally annular balloon 19 provided internally therearound, and arranged to expand inwardly towards the central shaft 11 on inflation. The balloon 19 communicates with an inflation port 21 located on the hub 13, by means of an inflation tube 22 extending along the channel 17 and into the sleeve 12.

Use of the device 10 in a surgical procedure will now be described with reference to FIGS. 3 to 9.

Referring first to FIG. 3, there is shown a vessel of a patient generally indicated 30, defined by vessel walls 31. An angioplasty guidewire 32 extends generally axially along the vessel 30, having previously been located therein during an intravascular angioplasty procedure. A undeployed stent 33, which has become prematurely detached from its delivery catheter during the angioplasty procedure, is located in the vessel 30. The stent 33 has a central cavity 34 through which the guidewire 32 extends, but is otherwise free-floating within the vessel 30. Both the stent 33 and its central cavity 34 are generally cylindrical.

The retrieval device 10 is introduced into the vessel 30, by means of a guiding catheter 35. As with the guidewire 32, the guiding catheter 35 will usually have been placed in position in the vessel 30 during the preceding angioplasty procedure. The device 10 is introduced through the catheter 35 such that the guidewire 32 passes through the aperture in the tip 15 of the central shaft 11 and into the channel 17, such that the device 10 can be maneuvered along the vessel 30 using the guidewire 32.

Figure 4:
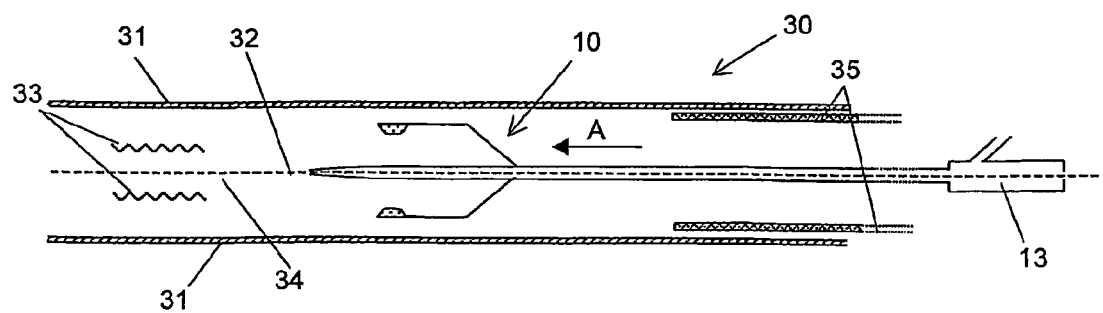

As can be seen from FIG. 4, the catheter 35 is retained in position whilst the device 10 is driven out of the catheter 35, and further into the vessel 30 towards the stent 33, as indicated by arrow A. This is controlled by the surgeon from the hub 13 end of the device 10, which remains externally of the vessel 30, and indeed externally of the patient.

Figure 5:
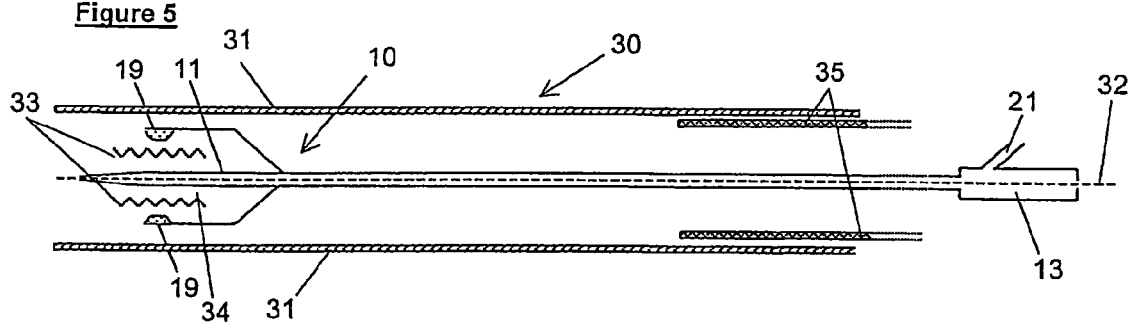

The device 10 is driven into the vessel 30 until the position shown in FIG. 5 is reached, where the outer circumference of the stent 33 is surrounded by the generally annular balloon 19, and the tip 15 of the central shaft 11 protrudes through the central cavity 34 of the stent 33. Inflation of the balloon 19 is then initiated by the introduction of 2 to 5 ml of radiographic contrast inflation fluid, via the inflation port 21 located on the hub 13, and along the inflation tube.

Figure 6:
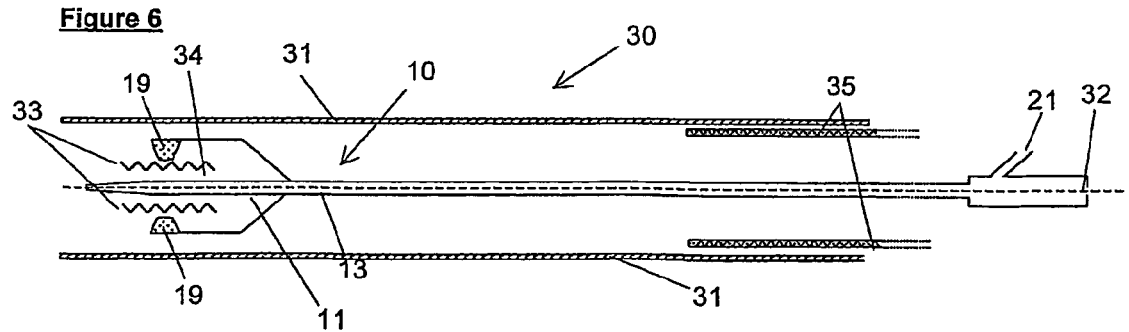
Figure 7:
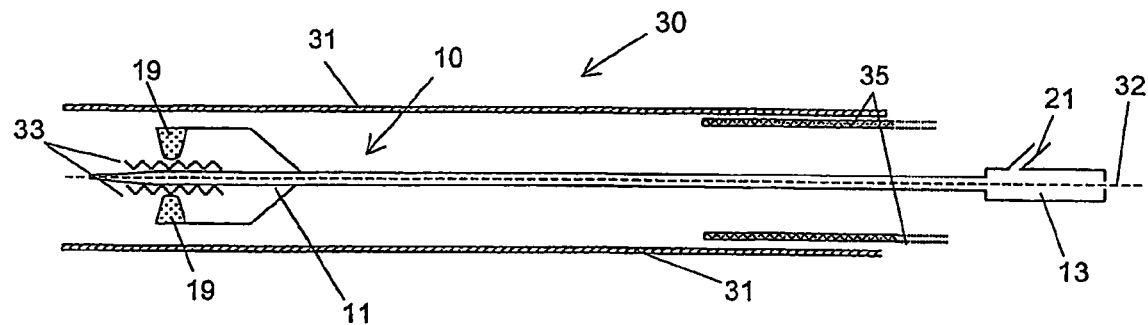

As is shown in FIG. 6, this causes the balloon 19 to expand inwardly toward the central shaft 11, until the balloon 19 bears against the outer circumference of the stent 33. Further inflation of the balloon 19, as shown in FIG. 7, compresses the stent 33 so that it is held between the balloon 19 and the central shaft 11.

Figure 8:
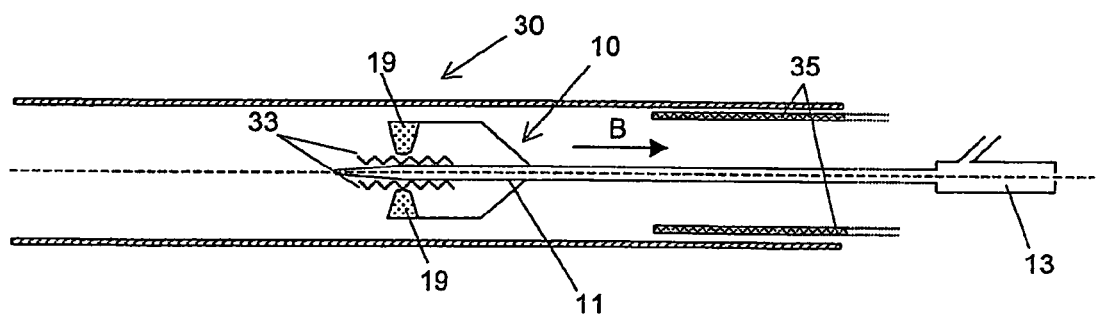
Figure 9:
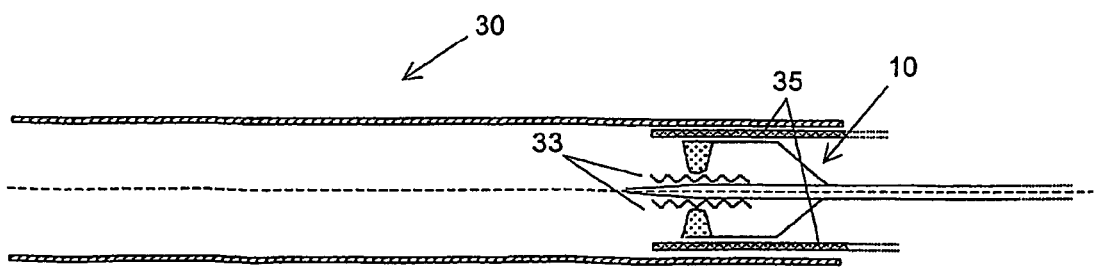

Referring now to FIG. 8, the device 10, with the stent 33 grasped firmly between the balloon 19 and the central shaft 11, is then maneuvered back toward the catheter 35, as indicated by arrow B. As before, this motion is controlled by the surgeon, from the hub 13 end of the device 10, which has remained externally of the patient throughout the procedure. Finally, as shown in FIG. 9, the combined stent 33 and device 10 assembly is withdrawn as one through the catheter 35, out of the vessel 30, and ultimately out of the patient. The catheter 35 and the guidewire 32 are usually left in position in the vessel 30, to enable subsequent angioplasty procedures.

The invention claimed is:

1. A device for retrieval of an intravascular stent from a vessel of a patient, said device comprising:
   a flexibly resilient central shaft having a tip, and an axial channel for receiving an angioplasty guidewire therein, said central shaft having a diameter sized such that said central shaft is received in a central cavity formed by a tubular body of said stent;
   balloon support means fixed to and extending from said central shaft and having a free end spaced therefrom, said balloon support means being a generally cylindrical sleeve spaced radially from and surrounding said central shaft and extending axially relative thereto to define an annular recess between said sleeve and said central shaft for receiving said tubular body of said stent; and generally annular inflatable balloon means provided at said free end of said balloon support means and arranged to expand inwardly towards said central shaft upon inflation;

whereby in use said device is positioned such that said tubular body of said stent to be retrieved is received in said annular recess, an outer surface of said stent is surrounded by said generally annular balloon means, said tip of said central shaft protrudes through said central cavity of said stent, and said balloon means is subsequently inflated to bear against said outer surface of said stent, thereby to compress said stent and hold said stent between said balloon means and said central shaft, such that said stent and said device can be withdrawn together from the vessel.

2. The device as claimed in claim 1, wherein said central shaft is generally cylindrical, having a uniform diameter along most of its length, and a short tapering section towards its tip.

3. The device as claimed in claim 1, further comprising a hub at an end of said central shaft distal from said inflatable balloon means.

4. The device as claimed in claim 3, wherein said hub has a port in fluid communication with said inflatable balloon means to enable inflation thereof by injection of an inflation fluid.

5. The device as claimed in claim 4, wherein said port is adapted to receive a syringe from which the inflation fluid is to be delivered.

6. The device as claimed in claim 4, wherein said inflation fluid is of radiographic contrast.

7. The device as claimed in claim 4, wherein inflation of said inflatable balloon means is effected by the injection of a volume of inflation fluid in the range of from 2 to 5 ml.

8. The device as claimed in claim 1, said device being adapted for delivery into and recovery from a vessel by means of a guiding catheter.

9. The device as claimed in claim 1, further comprising a guiding catheter for delivery of said device into a vessel, and subsequent recovery of said device therefrom.

10. The device as claimed in claim 1, wherein said central shaft is non-expandable.

11. A kit used during angioplasty procedures for retrieving an intravascular stent from a vessel of a patient, the kit comprising:

a guiding catheter positioned in the vessel of the patient; and a retrieval device slidable back and forth through the guiding catheter, the retrieval device including:

a flexibly resilient central shaft having a tip and an axial channel for receiving an angioplasty guidewire therein, the central shaft having a diameter sized such that the central shaft is received in a central cavity formed by a tubular body of the stent, a balloon support means fixed to and extending from the central shaft and having a free end spaced therefrom, the balloon support means being a generally cylindrical sleeve spaced radially from and surrounding the central shaft and extending axially relative thereto to define an annular recess between the sleeve and the central shaft for receiving the tubular body of the stent, and generally annular inflatable balloon means provided at the free end of the balloon support means, and arranged to expand inwardly towards the central shaft upon inflation, whereby in use, the device is moved through the guiding catheter such that the tubular body of the stent to be retrieved is received in the annular recess, an outer surface of the stent is surrounded by the generally annular balloon means, the tip of the central shaft protrudes through the central cavity of the stent, and the balloon means is subsequently inflated to bear against the outer surface of the stent, thereby to compress the stent, and hold the stent between the balloon means and the central shaft, such that the stent and device can be withdrawn together through the guiding catheter and from the vessel leaving the guidewire and guiding catheter in place in the vessel to enable subsequent angioplasty procedures.

* * * * *